(12) United States Patent
Young et al.

(10) Patent No.: US 8,622,886 B2
(45) Date of Patent: Jan. 7, 2014

(54) SURGICAL INSTRUMENT AND METHOD FOR THE TREATMENT OF URINARY INCONTINENCE

(75) Inventors: John Young, Staten Island, NY (US); Frank A. Nastasi, Hoboken, NJ (US); Jessica Liberatore, Marlboro, NJ (US)

(73) Assignee: Ethicon, Inc., Somerville, NJ (US)

( * ) Notice: Subject to any disclaimer, the term of this patent is extended or adjusted under 35 U.S.C. 154(b) by 450 days.

(21) Appl. No.: 12/724,768

(22) Filed: Mar. 16, 2010

(65) Prior Publication Data

US 2011/0230703 A1    Sep. 22, 2011

(51) Int. Cl.
   *A61F 2/02*         (2006.01)
(52) U.S. Cl.
   USPC ............................................. 600/30; 600/29
(58) Field of Classification Search
   USPC .................. 600/29–32, 37; 606/139, 144–148
   See application file for complete search history.

(56) References Cited

U.S. PATENT DOCUMENTS

| | | | |
|---|---|---|---|
| 3,182,662 A | 5/1965 | Shirodkar | |
| 4,265,231 A | 5/1981 | Scheller et al. | |
| 4,509,516 A | 4/1985 | Richmond | |
| 5,032,508 A | 7/1991 | Naughton et al. | |
| 5,112,344 A | 5/1992 | Petros | |
| 5,281,237 A | 1/1994 | Gimpelson | |
| 5,383,904 A | 1/1995 | Totakura et al. | |
| 5,899,909 A | 5/1999 | Claren et al. | |
| 6,024,690 A | 2/2000 | Lee et al. | |
| 6,099,538 A | 8/2000 | Moses et al. | |
| 6,273,852 B1 | 8/2001 | Lehe et al. | |
| 6,475,139 B1 | 11/2002 | Miller | |
| 6,494,887 B1 | 12/2002 | Kaladelfos | |
| 6,605,097 B1 | 8/2003 | Lehe et al. | |
| 6,612,977 B2 | 9/2003 | Staskin et al. | |
| 6,638,211 B2 | 10/2003 | Suslian et al. | |
| 6,641,525 B2 | 11/2003 | Rocheleau et al. | |
| 6,652,450 B2 | 11/2003 | Neisz et al. | |

(Continued)

FOREIGN PATENT DOCUMENTS

| | | |
|---|---|---|
| DE | 10/2004015720 A1 | 10/2005 |
| EP | 0598976 B1 | 7/2000 |

(Continued)

OTHER PUBLICATIONS

International Search Report mailed Jul. 1, 2011 for corresponding Patent Application No. PCT/US2011/028290.

(Continued)

*Primary Examiner* — Charles A Marmor, II
*Assistant Examiner* — Laura Fajardo

(57) ABSTRACT

A surgical assembly including an introducer having a handle portion and a needle portion, and at least a first retaining device extending outwardly therefrom. The assembly also includes first and second sheath elements each having a proximal end, a closed tissue penetrating distal end, a channel extending therein and a side aperture extending into the channel, and an implant having first and second ends coupled to the proximal ends of the sheath elements respectively. Channels of the first and second sheath elements are dimensioned to slidably receive therein through the side aperture the needle portion of the introducer, and for each of the first and second sheath elements when the needle portion of the introducer is so received therein, the peripheral edge of the side aperture is capable of being removably coupled to the retaining device to thereby fixedly secure the sheath element to the introducer.

15 Claims, 7 Drawing Sheets

(56) References Cited

U.S. PATENT DOCUMENTS

| | | | |
|---|---|---|---|
| 6,752,081 B2 | 6/2004 | Callahan et al. | |
| 6,808,486 B1* | 10/2004 | O'Donnell | 600/30 |
| 6,911,003 B2 | 6/2005 | Anderson et al. | |
| 7,204,802 B2* | 4/2007 | De Leval | 600/30 |
| 7,244,259 B2 | 7/2007 | Smith et al. | |
| 7,261,723 B2 | 8/2007 | Smith et al. | |
| 7,371,245 B2 | 5/2008 | Evans et al. | |
| 7,611,454 B2 | 11/2009 | De Leval | |
| 2002/0050277 A1 | 5/2002 | Beyar | |
| 2002/0055748 A1 | 5/2002 | Gellman et al. | |
| 2002/0099260 A1 | 7/2002 | Suslian et al. | |
| 2002/0151762 A1 | 10/2002 | Rocheleau et al. | |
| 2002/0156489 A1 | 10/2002 | Gellman et al. | |
| 2003/0171644 A1* | 9/2003 | Anderson et al. | 600/29 |
| 2004/0267088 A1 | 12/2004 | Kammerer | |
| 2005/0075660 A1* | 4/2005 | Chu et al. | 606/190 |
| 2005/0177022 A1 | 8/2005 | Chu et al. | |
| 2008/0139877 A1* | 6/2008 | Chu et al. | 600/30 |
| 2008/0287731 A1* | 11/2008 | Kuntz | 600/30 |
| 2009/0306459 A1 | 12/2009 | De Leval | |

FOREIGN PATENT DOCUMENTS

| | | |
|---|---|---|
| EP | 1159921 A2 | 12/2001 |
| EP | 1342450 B1 | 9/2003 |
| WO | WO 90/03766 A1 | 4/1990 |
| WO | WO 2004/008977 A1 | 1/2004 |

OTHER PUBLICATIONS

Nickel, R.F. et al., "Evaluation of a Transpelvic Sling Procedure With and Without Colposuspension for Treatment of Female Dogs With Refractory Urethral Sphincter Mechanism Incompetence" Veterinary Surgery 27:94-101 (1998).

De Leval, J., "Novel Surgical Technique for the Treatment of Female Stress Urinary Incontinence: Transobturator Vaginal Tape Inside-Out", European Urology 44 (2003) 724-730.

Hermieu, J. et al., Progres en Urologie (2003), 13, 115-117.

* cited by examiner

SURGICAL INSTRUMENT AND METHOD FOR THE TREATMENT OF URINARY INCONTINENCE

BACKGROUND OF THE INVENTION

1. Field of the Invention

The present invention relates generally to devices and methods for the treatment of female urinary incontinence, and more particularly, to an inserter and sheath combination and method particularly suitable for placing a sub-urethral sling.

2. Background Discussion

Women account for more than 11 million incontinence cases, with a majority of those women suffering from stress urinary incontinence (SUI). Women with SUI involuntarily lose urine during normal daily activities and movements, such as laughing, coughing, sneezing and regular exercise.

SUI may be caused by a functional defect or weakened tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle and shy away from social situations.

One device and method for treating female urinary stress incontinence is described in detail in U.S. Pat. No. 5,899,909, which is incorporated herein by reference in its entirety. This patent discloses a surgical instrument comprising a shank having a handle at one end and connecting means at the other end to receive, one at a time, two curved needle-like elements which each are connected at one end to respective ends of a mesh intended to be implanted into the body. In practice, the mesh is passed into the body via the vagina first at one end and then at the other end, at one side and the other, respectively, of the urethra to form a loop around the urethra, located between the urethra and vaginal wall. The mesh is extended over the pubis and through the abdominal wall and is tightened. The mesh ends are cut at the abdominal wall, and the mesh is left implanted in the body. This trans-vaginal procedure is exemplified by the TVT product sold by the Gynecare franchise of Ethicon Inc., a Johnson & Johnson Company, of Somerville, N.J., USA. In this procedure two 5 mm needles pass a PROLENE mesh trans-vaginally and through the abdomen to create a tension-free support under the mid-urethra.

Sub-urethral slings have also been placed by a different approach wherein a needle is passed first though the abdominal wall along the same path as described above, and eventually exiting through the vaginal incision. The tape is then coupled to the needle in some manner, and pulled back through the body from the vaginal incision and out through the abdominal incision. The chosen approach, vaginal or abdominal, will often depend on the preferences of the surgeon.

Yet another approach for implanting a sub-urethral sling has also been recently developed in which the implanted sling extends from beneath the urethra, and out through the obturator hole on either side. This "transobturator" procedure may involve inserting an appropriately configured needle from a vaginal incision and subsequently out through the obturator hole, or vice versa. The former technique (an "inside-out" approach) and associated instruments are described in detail in U.S. Pat. Nos. 7,611,454, 7,204,802, and 7,261,723, and U.S. Patent Publication No. 2009/0306459, which are incorporated herein by reference in their entirety. As illustrated in U.S. Pat. No. 7,261,723, this technique may be performed using a surgical instrument including a surgical passer or introducer and tube elements applied over the ends of the surgical passers that are coupled to the tape to be implanted under the urethra.

On problem associated with products including a combination surgical passer and tube or sheath element is ensuring a proper fit between the surgical passer and tube element so that the tube element (which is coupled to the implant) is suitably secured to surgical passer throughout the procedure, but can be readily removed from the surgical passer after it has been properly passed through the body to allow final placement of the implant. Known devices have either relied exclusively on a frictional or interference fit between the two pieces along at least a portion of their respective lengths, and/or some type of complementary interlocking recess/projection along their respective lengths of the type described in the '723 patent. For devices that rely exclusively on a frictional fit, they can either be subject to relative movement during the procedure if the friction connection is too weak, or otherwise be difficult or cumbersome for a surgeon to separate following passage of the surgical passer through the body. A complementary interlocking recess/projection requires a unique surgical passer and tube design that adds to the manufacturing and device costs of the product.

Thus, it would be desirable to provide an improved surgical assembly in which the surgical introducer and sheath are secured together in a manner that allows for suitable coupling during implantation, yet allows for easy decoupling following desired placement of the sub-urethral implant, and that has reduced costs.

SUMMARY OF THE INVENTION

The present invention provides a surgical assembly including a surgical introducer having a handle portion and a needle portion extending outwardly to a free distal end from a first end of the handle portion, and having at least a first retaining device extending outwardly therefrom. The assembly further includes first and second sheath elements each having a proximal end, a closed tissue penetrating distal end, a channel extending therein from an opening at the proximal end to the closed distal end, and a side aperture defined by a peripheral edge and extending into the channel; and also an implant made of a substantially flat, flexible, biocompatible material, and having first and second ends coupled to the proximal ends of the first and second sheath elements respectively. The channels of the first and second sheath elements are dimensioned to slidably receive therein through the side aperture the needle portion of the introducer, and for each of the first and second sheath elements when the needle portion of the introducer is so received therein, the peripheral edge of the side aperture is capable of being removably coupled to the retaining device to thereby fixedly secure the sheath element to the introducer.

The retaining device may be a projection extending outwardly from the handle portion of the introducer, and may project both outwardly and in a direction toward a proximal end of the handle. In one embodiment, the needle element has an outer diameter of approximately 3.0 mm and the channel of the sheath element has a diameter of approximately 3.2 mm. The sheath element may further have an outer diameter of approximately 4.2 mm.

In another embodiment, the needle element outer diameter is substantially constant along the length of the needle element, and the channel diameter is substantially constant along the length of the sheath element. The surgical passer may be comprised of stainless steel and the sheath element may be comprised of a medical grade plastic selected from the group consisting of urethane, polyethylene, and polypropylene.

In yet another embodiment, the needle portion of the surgical passer has a contour, and the sheath element is configured to follow the surgical passer contour. The side apertures of the sheath elements may also be located in a proximal end region of the sheath elements.

Also provided is a surgical assembly including a surgical introducer having a handle portion having opposing distal and proximal ends, and a needle portion having a substantially constant outer diameter and extending outwardly to a free distal end from the distal end of the handle portion, and having at least a first retaining device extending outwardly from the handle portion. The assembly further includes first and second sheath elements each having a proximal end, a closed tissue penetrating distal end, a channel extending therein from an opening at the proximal end to the closed distal end, and a side aperture defined by a peripheral edge extending into the channel at a predetermine point along a length thereof; and also an implant made of a substantially flat, flexible, biocompatible material, and having first and second ends coupled to the proximal ends of the first and second sheath elements respectively. The channels of the first and second sheath elements are dimensioned to slidably receive therein through the side aperture the needle portion of the introducer, and for each of the first and second sheath elements when the needle portion of the introducer is so received therein, the peripheral edge of the side aperture is capable of being removably coupled to the retaining device to thereby fixedly secure the sheath element to the introducer.

The retaining device may be a projection extending outwardly and toward the proximal end of the handle portion, and the assembly may include first and second retaining devices positioned on opposing sides of the handle portion.

These and other features and advantages of the present invention will become apparent from the following more detailed description, when taken in conjunction with the accompanying drawings which illustrate, by way of example, the principles of the invention.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways.

Figure 1:
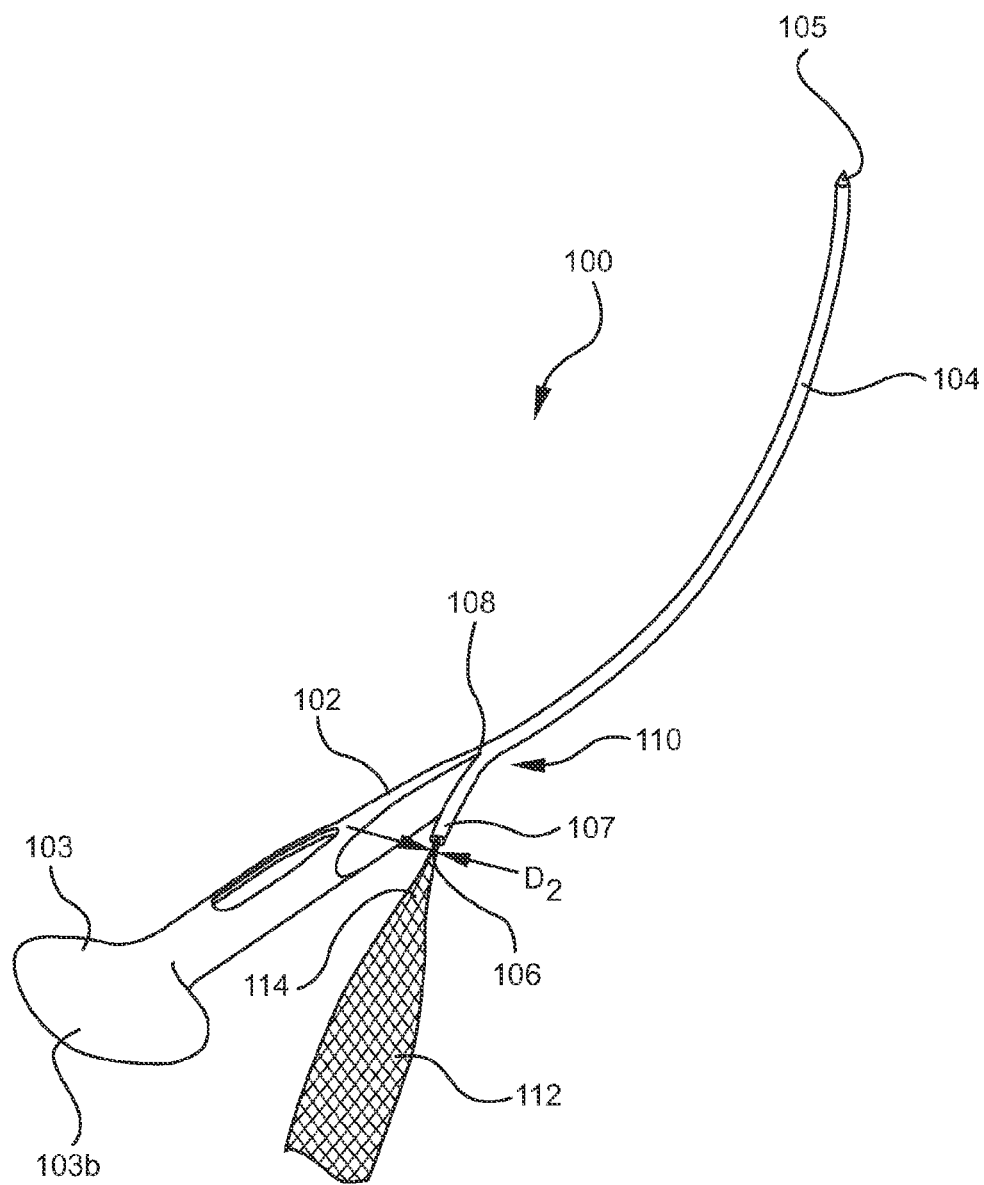
FIG. 1 illustrates a surgical assembly according to the present invention.
Figure 2A:
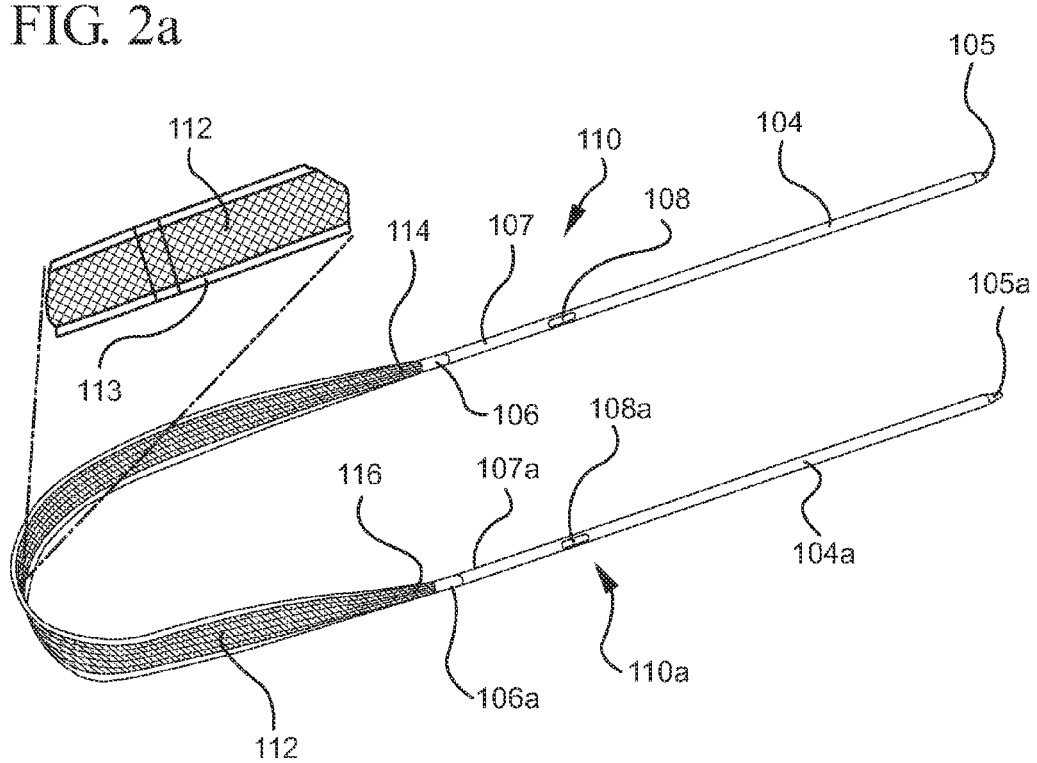
FIGS. 2a and 2b illustrate separately the introducer and sheath of the surgical assembly of FIG. 1.
Figure 2B:
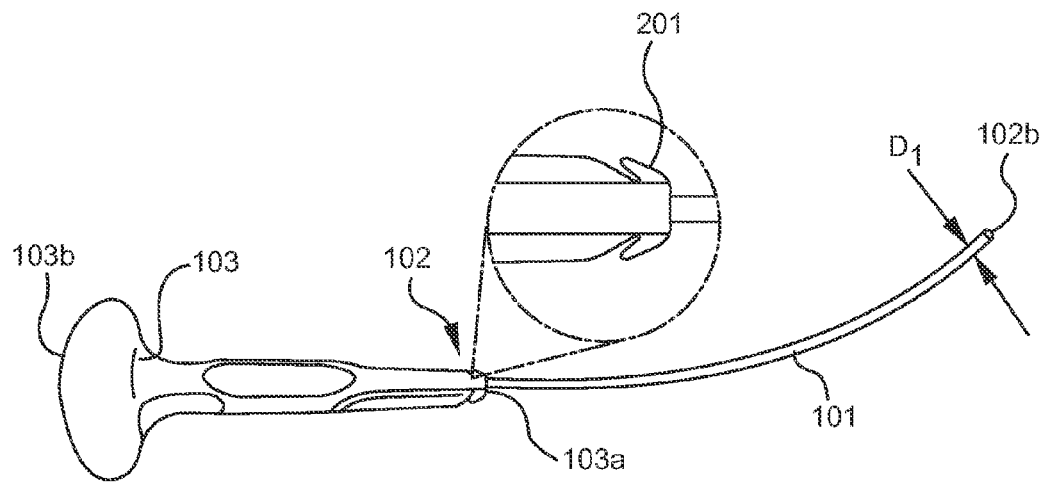
Figure 3:
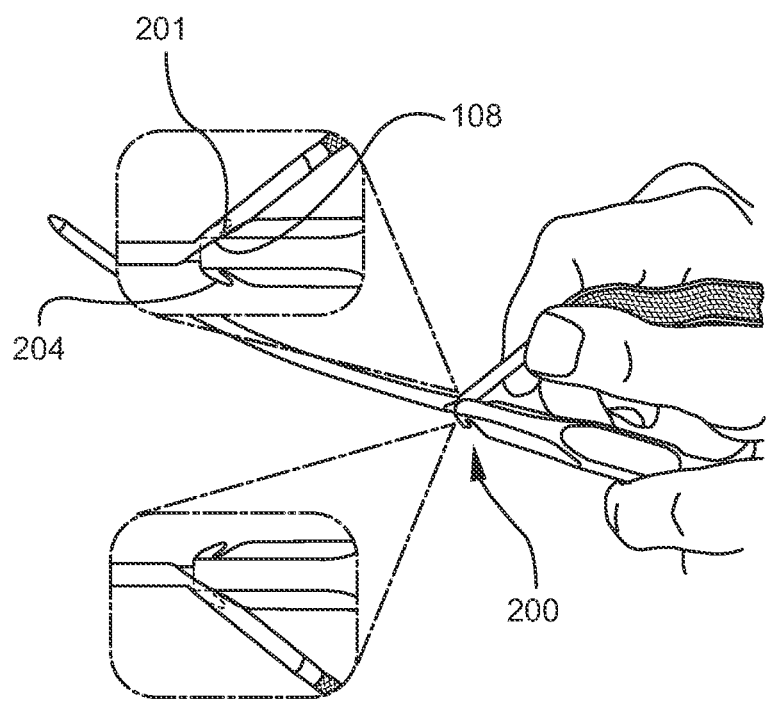
FIG. 3 illustrates in greater detail the mechanism for securing the introducer to the sheath.

FIGS. 1-3 illustrate one embodiment of a surgical assembly according to the present invention. The surgical assembly 100 includes an introducer 102 having needle element 101 and a handle portion 103 having a distal end 103a and a proximal end 103b, and first and second sheath elements 104, 104a. The needle element extends outwardly from the handle to a distal end 102b, that is preferably blunt as illustrated in FIG. 2b. The sheath elements are tube type elements each having a tissue penetrating distal end 105, 105a and a channel extending from an opening 106, 106a at the proximal end 107, 107a to the closed distal end 105, 105a. As illustrated more clearly in FIG. 2a, the sheath elements 104, 104a also each include a side hole or aperture 108, 108a in one side thereof in the proximal end region 110, 110a. A biocompatible tape or mesh 112 to be implanted beneath the urethra of a patient includes first 114 and second 116 ends which are secured respectively to the proximal ends 107, 107a of the sheath elements as shown in FIG. 2a. Preferably, the ends 114, 116 are inserted into the proximal end openings 106, 106a of the sheath elements and heat and pressure is applied to fixedly join the two. The mesh implant 112 is preferably substantially enclosed within a thin polypropylene sheath 113 as shown in the enlarged portion of FIG. 2a. The polypropylene sheath may include two separate sheath portions applied over both ends and overlapping in the middle region so that, following implantation of the mesh, they can readily be removed from respective ends of the mesh. In one embodiment, the mesh implant is a polypropylene mesh, but it may be comprised of any suitable biocompatible material.

The sheath element channels have an inner diameter dimensioned to receive therein the needle element 101 of the introducer 102. Preferably, the surgical assembly includes a single introducer that is receivable within both the first and second sheath element channels, although a second introducer could also be provided in the surgical assembly.

The outer diameter $D_1$ of the needle element 101 of the surgical introducer 102 is designed relative to the diameter $D_2$ of the channel of the sheath or tube element to have a clearance fit such that the surgical passer is readily insertable within the tube element, and removably therefrom with little frictional resistance. In this manner, following passage of the surgical assembly through the body as described below, the introducer can readily be removed from the sheath element without moving or otherwise disturbing the position of the sheath element and attached implant. In a preferred embodiment, the diameter $D_1$ is approximately 3 mm and the diameter $D_2$ is approximately 3.2 mm.

As the introducer is so readily removable/slidable relative to the sheath element, the surgical assembly further includes a retaining device 200 to ensure that the sheath elements 104, 104a can be fixedly, but removably secured to the introducer 102 during the procedure, which includes passage of the surgical assembly through the body. As is best shown in FIG. 3, in a preferred embodiment, the retaining device 200 includes one or more projections 201 extending outwardly from the introducer, and preferably from the handle portion 103 of the introducer. The projection(s) 201 are located along the length of the introducer at a position where, when the sheath element 104 is slidably received over the needle element 101, as shown in FIG. 1, it is substantially aligned with the side aperture 108 of the sheath element. In this manner, the retaining element 200 can be inserted into the side aperture to engage the edge or periphery defining the side aperture to thereby hold the sheath in place relative to the introducer. In a preferred embodiment, the retaining elements project both outwardly and also in a direction towards the proximal end 103b of the introducer. This enables the retaining element to more securely grasp the sheath element and prevent it from slipping off the distal end of the needle element.

In a preferred embodiment, the sheath element is made of a high density polyethylene (plastic) material that allows the sheath to conform to necessary applied forces without loss of intended function, and still return to it approximate original shape.

Figure 5A:
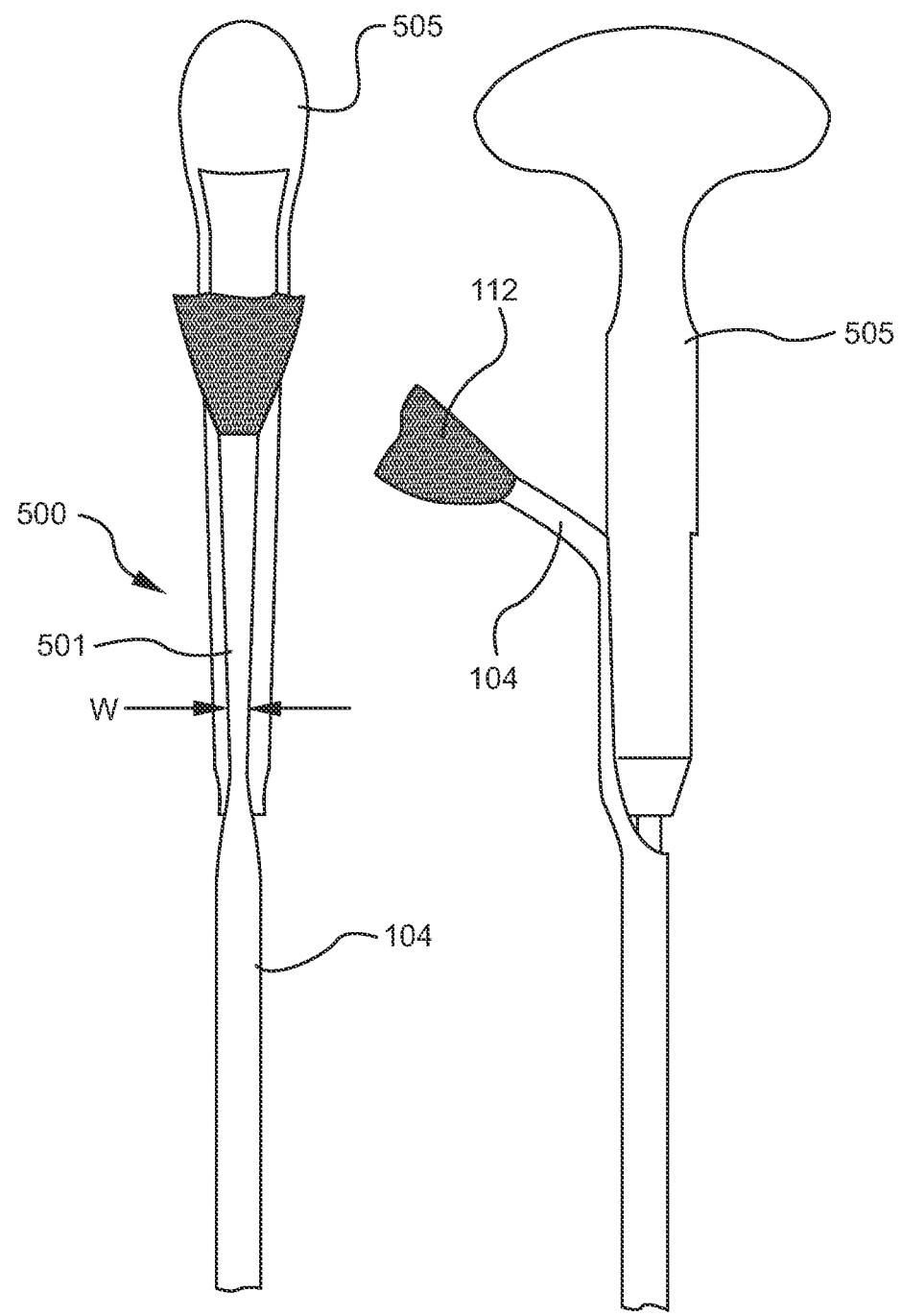
FIGS. 5a and 5b illustrate alternate embodiments of a retaining device of a surgical assembly according to the present invention.
Figure 5B:
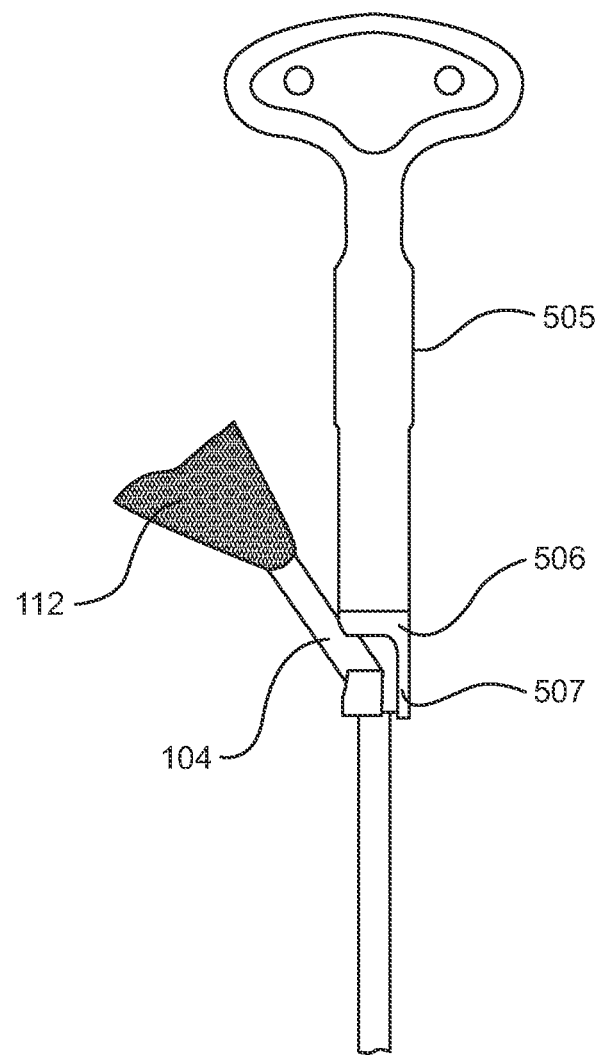

Alternate embodiments of a retaining device are shown in FIGS. 5a and 5b. FIG. 5a illustrates a retaining device 500 comprised of one or more channels or grooves 501 extending longitudinally along at least a portion of the handle portion of the introducer. The channel or groove has a width w that is less than the outer diameter of the sheath element. Due to the hollow structure and flexible nature of the sheath element, it can be compressed slightly and forced into the groove, thereby securing it in place relative to the introducer. Referring now to another embodiment illustrated in FIG. 5b, the handle portion 505 of the introducer may be modified to include a rotatable collar 506 at the distal end. The collar 506 includes a groove 507 or the like therethrough having an exterior opening dimensioned to receive therein a portion of the sheath element. Once received the collar can be rotated to enclose the portion of the sheath element in a bayonet style mechanism, thereby securing it to the introducer.

A method of using the above-described surgical instrument will now be described in detail with reference to FIGS. 4a-4d. The patient is placed in the lithotomy position with the hips flexed, preferably no more than 60 degrees, and the bladder emptied. A small paraurethral incision is made over the mid-urethra to position the tip of the sheath element. A sagital incision is then made about 1.5 cm in length starting at approximately 1.0 cm cephalad from the urethral meatus.

The incision will be positioned over the mid-urethral zone and will allow for subsequent passage of the implant. Two small paraurethral dissections (approximately 0.5 cm) are then made to accommodate the tips of the sheath elements of the surgical assembly.

Figure 4A:
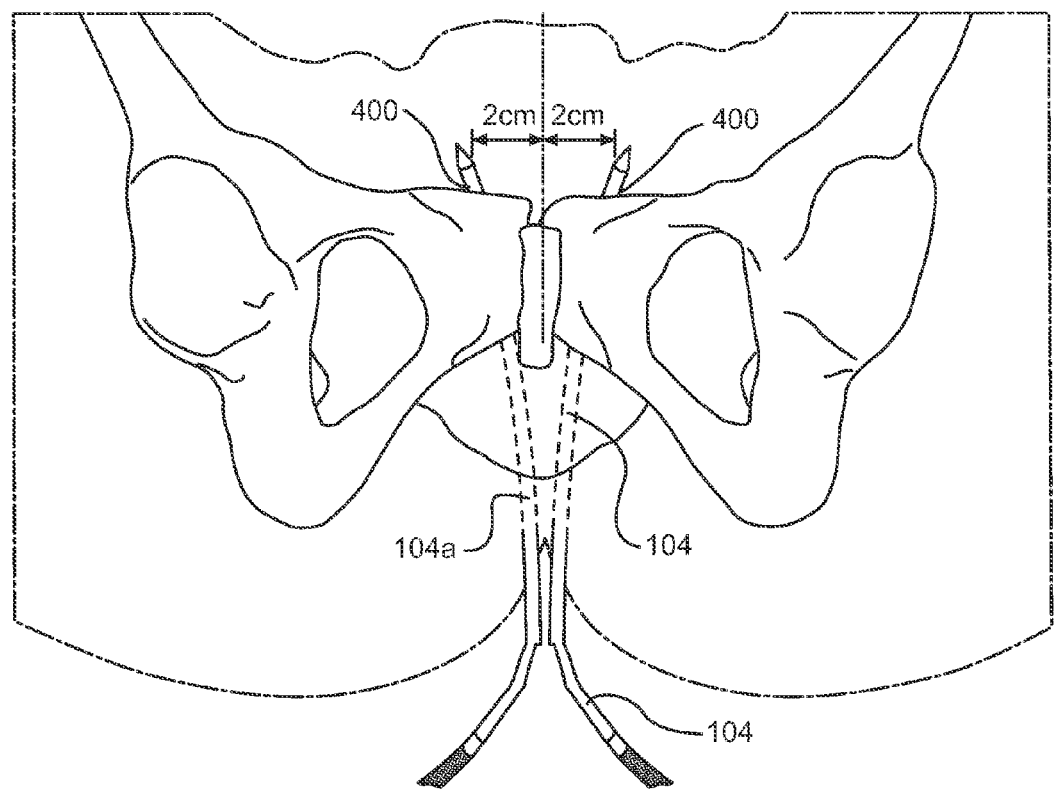
FIGS. 4a-4d illustrate an exemplary passage through the body of the surgical assembly of FIG. 1.

The two exit points 400 are then identified and marked. Preferably, these exit points are 2-2.5 cm on each side of the mid-line, immediately above the pubic symphasis as shown in FIG. 4a, and are no more than 2.5 cm from the mid-line to avoid the inferior epigastric vessels, and near the mid-line and close to the superior aspect of the pubic bone 405 to avoid anatomic structures in the inguinal area and lateral pelvic sidewall.

Once the bladder is drained a catheter guide or the like 401 can be used to allow contra-lateral displacement of the bladder 402, bladder neck and urethra away from the tip of the surgical assembly as it is passed through the retropubic space 403.

Figure 4B:
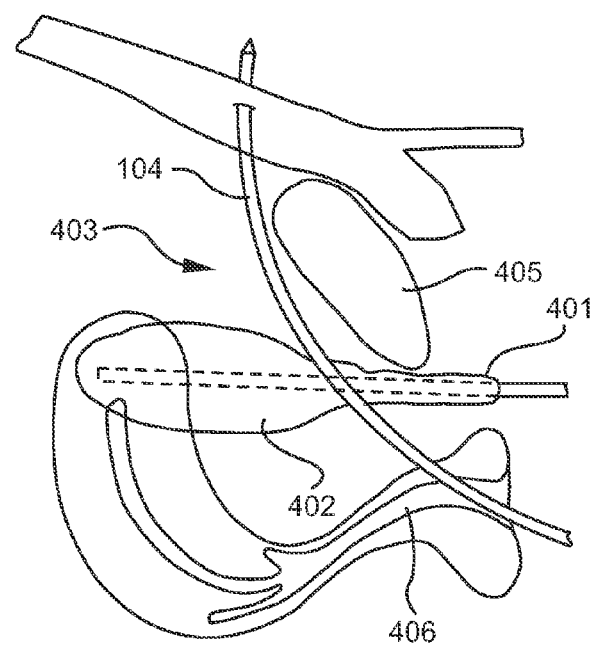

One of the sheath elements 104 is then slidably engaged over the needle element 101 of the introducer 102, and the side aperture of the sheath element engaged with the retaining element as described above. After ensuring lateral displacement of the bladder with the catheter guide, the handle of the surgical assembly is held and the tip of the surgical assembly is passed paraurethrally through the urogenital diaphragm at the level of the midurethra. Initial insertion of the surgical assembly is controlled by using the tip of the index finger, which is placed in the vagina 406 under the anterior vaginal wall, just lateral to the suburethral incision. With the curved part of the assembly resting in the palm of the hand, the assembly is passed through the urogenital diaphragm into the retropubic space. The tip is then guided through the retropubic space staying as close as possible to the back of the pubic symphysis or pubic bone 405 until the tip reaches the abdominal exit point 400 as shown in FIGS. 4a and 4b.

The tip of the surgical assembly is then grasped and held in place with a suitable clamp or other instrument, and the sheath element is disengaged from the introducer by uncoupling the sheath element from the retaining element. The introducer is then retracted and removed from the body while leaving the sheath element in place within the body as shown in FIG. 4a. The procedure is then repeated on the other side of the body, and with the sheath elements in place in the body (before final placement of the implant), the catheter is removed and bladder integrity confirmed.

Figure 4C:
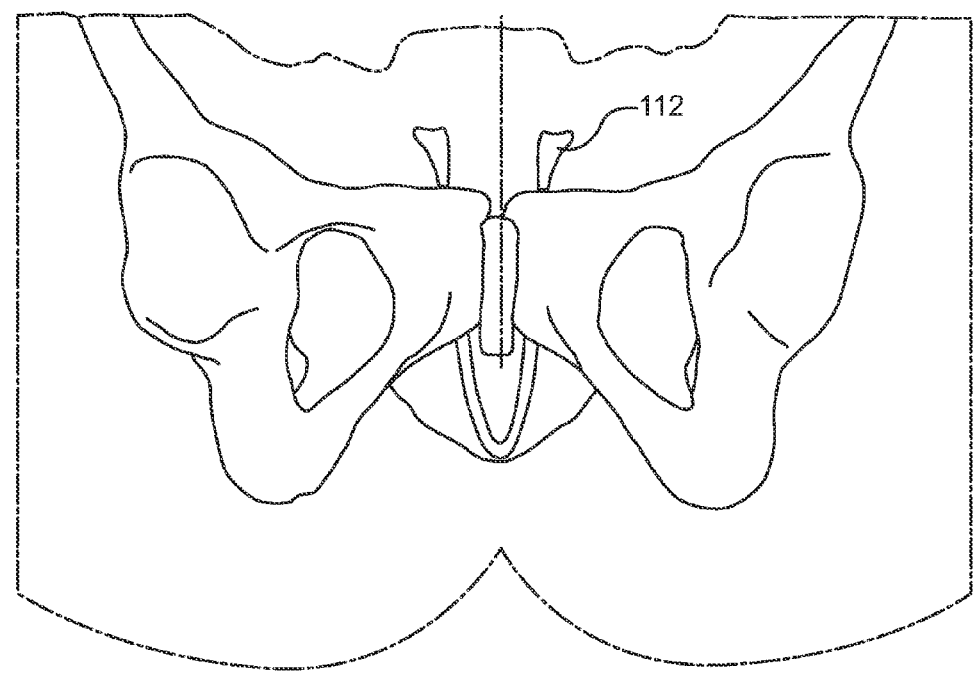
Figure 4D:
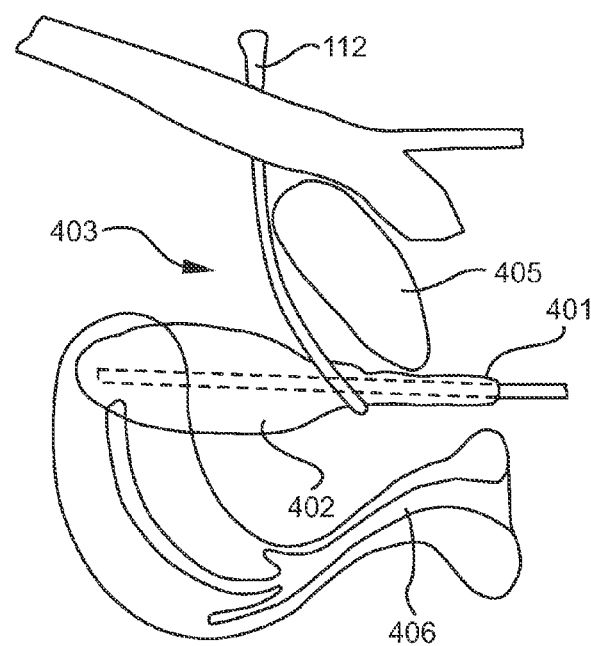

Both sheath elements are then pulled entirely through the abdominal exit points so that the implant is placed under the mid-urethra, and the implant cut in proximity to the sheath elements as shown in FIG. 4c-4d. The implant is then adjusted in a well known manner, the polypropylene sheaths removed from the ends of the implant, and the implant cut in proximity to the abdominal exit points. The vaginal incision and abdominal incisions are then closed and the implant left in place.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A surgical assembly comprising:
a surgical introducer having a handle portion and a needle portion extending outwardly to a free distal end from a first end of the handle portion, and having at least a first retaining device having a projection extending outwardly from the handle portion to a tapered free distal end and in a direction toward a proximal end of the handle;
first and second sheath elements each having a proximal end, a closed distal end that is tapered and capable of penetrating tissue, a channel extending therein from an opening at the proximal end to the closed distal end, and a side aperture extending into said channel, said side aperture being defined by a peripheral edge and dimensioned to receive therethrough the projection of the first retaining device;
an implant comprised of a substantially flat, flexible, biocompatible material, and having first and second ends coupled to the proximal ends of the first and second sheath elements respectively;
wherein the channels of the first and second sheath elements are dimensioned to slidably receive therein through the side aperture the needle portion of the introducer, and wherein for each of the first and second sheath elements when the needle portion of the introducer is so received therein, the sheath element completely encloses therein at least the distal free end of the needle portion, and the peripheral edge of the side aperture is capable of being removably coupled to the retaining device to thereby prevent sliding movement of the sheath element relative to the introducer.

2. The surgical assembly according to claim 1, wherein the needle portion has an outer diameter of approximately 3.0 mm and the channel of the sheath element has a diameter of approximately 3.2 mm.

3. The surgical assembly according to claim 2, wherein the sheath element has an outer diameter of approximately 4.2 mm.

4. The surgical assembly according to claim 2, wherein the needle portion outer diameter is substantially constant along the length of the needle portion, and wherein the channel diameter is substantially constant along the length of the sheath element.

5. The surgical assembly according to claim 4, wherein the needle portion is comprised of stainless steel and the sheath element is comprised of a medical grade plastic selected from the group consisting of urethane, polyethylene, and polypropylene.

6. The surgical assembly according to claim 1, wherein the needle portion has a contour, and wherein the sheath element is configured to follow said needle portion contour.

7. The surgical assembly according to claim 1, wherein the side apertures of the sheath elements are located in a proximal end region of the sheath elements.

8. A surgical assembly comprising:
a surgical introducer having a handle portion having opposing distal and proximal ends, and a needle portion having a substantially constant outer diameter and extending outwardly to a free distal end from the distal end of the handle portion, and having at least a first retaining device having a projection extending outwardly from the handle portion to a tapered free distal end and in a direction toward the proximal end of the handle;
first and second sheath elements each having a proximal end, a closed distal end that is tapered and capable of penetrating tissue, a channel extending therein from an opening at the proximal end to the closed distal end, and a side aperture extending into said channel at a predetermined point along a length thereof, said side aperture being defined by a peripheral edge and dimensioned to receive therethrough the first retaining device;
an implant comprised of a substantially flat, flexible, biocompatible material, and having first and second ends coupled to the proximal ends of the first and second sheath elements respectively;
wherein the channels of the first and second sheath elements are dimensioned to slidably receive therein through the side aperture the needle portion of the introducer, and wherein, the needle portion of the introducer is removably received within the first sheath element and the peripheral edge of the side aperture of the first sheath element is removably coupled to the retaining device to thereby prevent sliding movement of the first sheath element relative to the introducer.

9. The surgical assembly according to claim 8, including first and second retaining devices positioned on opposing sides of the handle portion.

10. The surgical assembly according to claim 8, wherein the needle portion has an outer diameter of approximately 3.0 mm and the channel of the sheath element has a diameter of approximately 3.2 mm.

11. The surgical assembly according to claim 10, wherein the sheath element has an outer diameter of approximately 4.2 mm.

12. The surgical assembly according to claim 8, wherein the channel of the sheath element has a substantially constant diameter along its length.

13. The surgical assembly according to claim 8, wherein the needle portion is comprised of stainless steel and the sheath element is comprised of a medical grade plastic selected from the group consisting of urethane, polyethylene, and polypropylene.

14. The surgical assembly according to claim 8, wherein the needle portion has a contour, and wherein the sheath element is configured to follow said needle portion contour.

15. The surgical assembly according to claim 8, wherein the side apertures of the sheath elements are located in a proximal end region of the sheath elements.

* * * * *